United States Patent [19]

Bellotti et al.

[11] Patent Number: 4,655,753

[45] Date of Patent: Apr. 7, 1987

[54] CONNECTION DEVICE

[75] Inventors: Marc C. Bellotti, Winnetka; William J. Schnell, Libertyville, both of Ill.

[73] Assignee: Baxter Travenol Laboratories, Inc., Deerfield, Ill.

[21] Appl. No.: 802,787

[22] Filed: Nov. 27, 1985

[51] Int. Cl.⁴ ............................................... A61M 5/00
[52] U.S. Cl. .................................... 604/283; 604/29; 604/905
[58] Field of Search ............... 604/283, 29, 411, 410, 604/905, 244; 250/455.1

[56] References Cited

U.S. PATENT DOCUMENTS

| | | |
|---|---|---|
| 4,405,315 | 9/1983 | Aandt ..................................... 604/29 |
| 4,412,834 | 11/1983 | Kulin et al. ............................ 604/29 |
| 4,500,788 | 2/1985 | Kulin et al. ...................... 604/283 X |
| 4,541,829 | 9/1985 | Munsch et al. ................... 604/29 X |

Primary Examiner—Stephen C. Pellegrino
Attorney, Agent, or Firm—Paul C. Flattery; Daniel D. Ryan

[57] ABSTRACT

A device automatically uncouples two connectors and forms a new coupling between one of the connectors and another connector in a aseptic manner, without touch contamination from the user. The device automatically readies itself for use after every operation.

23 Claims, 11 Drawing Figures

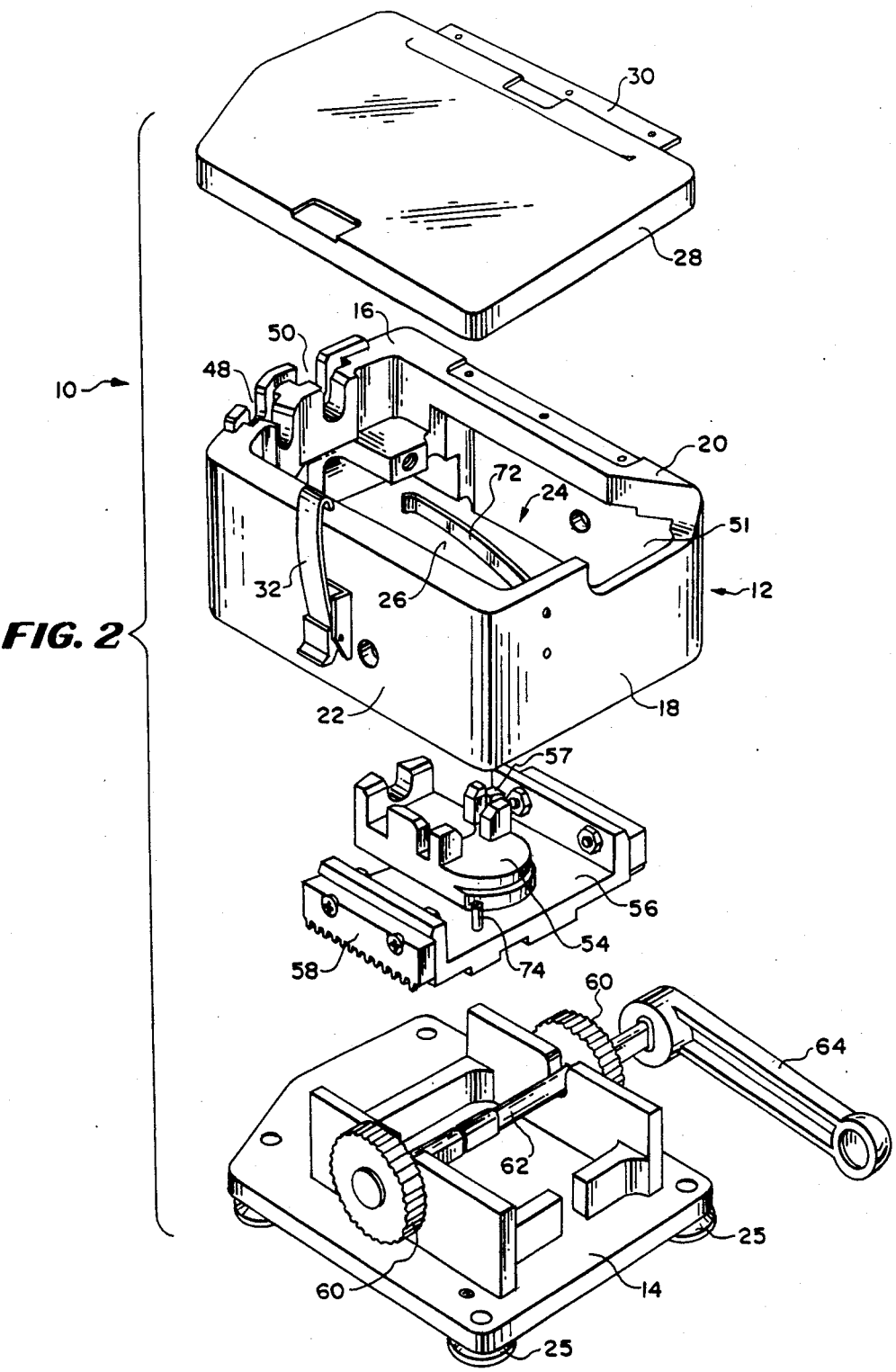

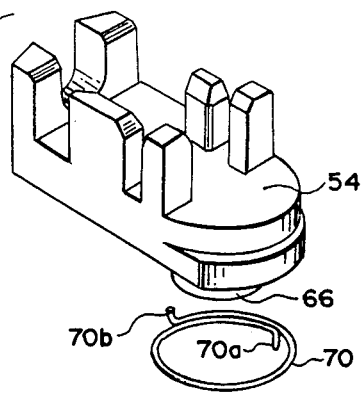
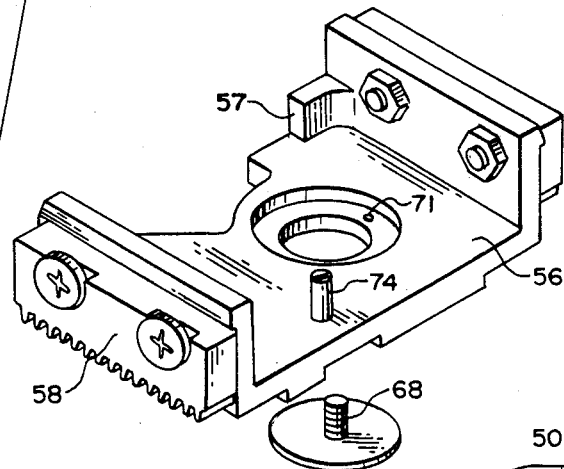
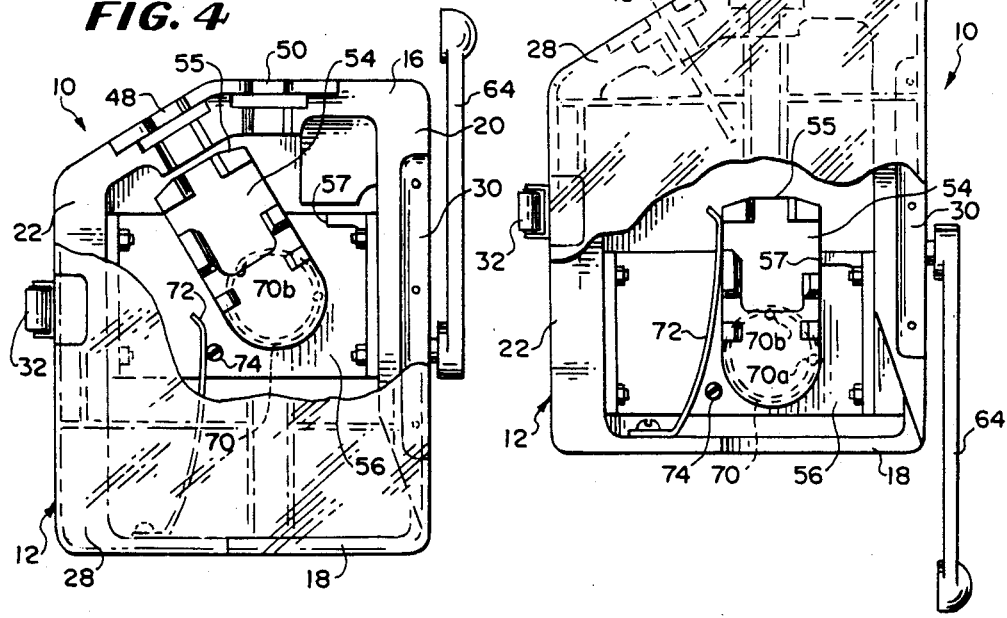

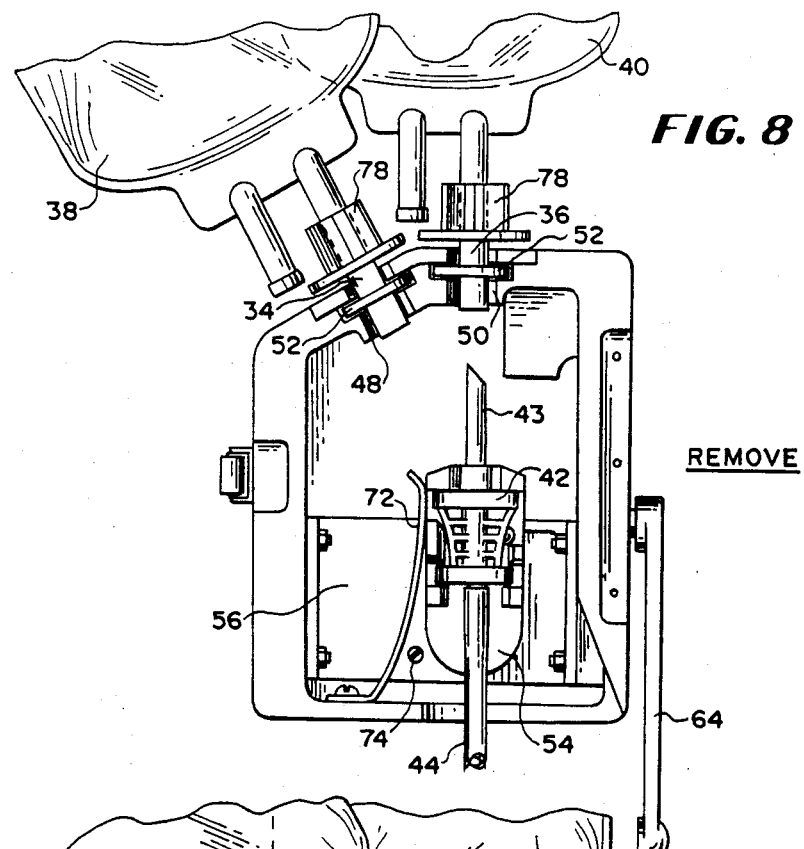
FIG. 8 REMOVE
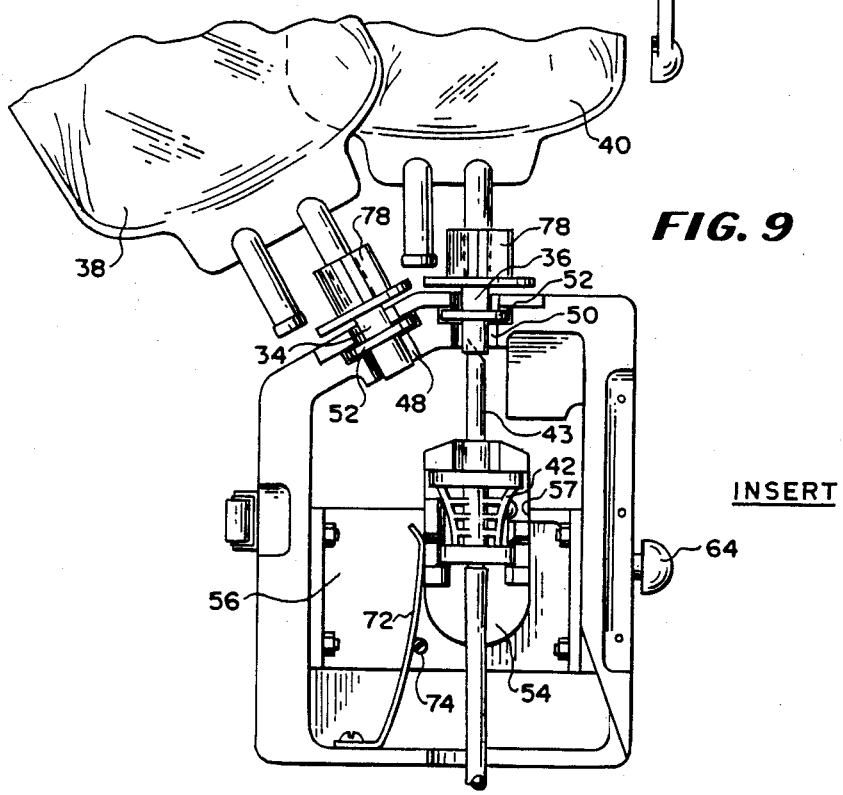
FIG. 9 INSERT

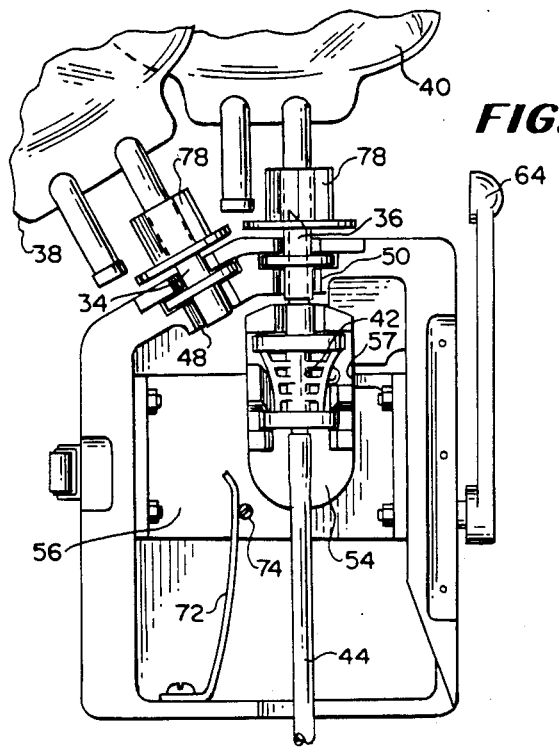
FIG. 10
EXCHANGE
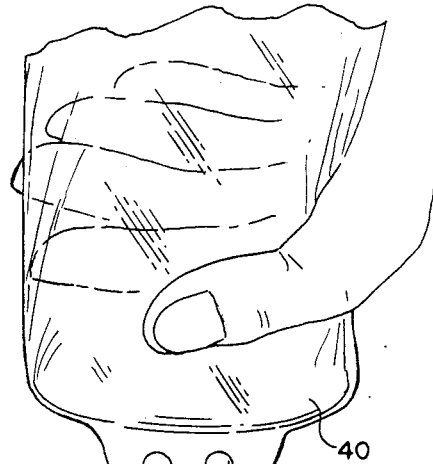
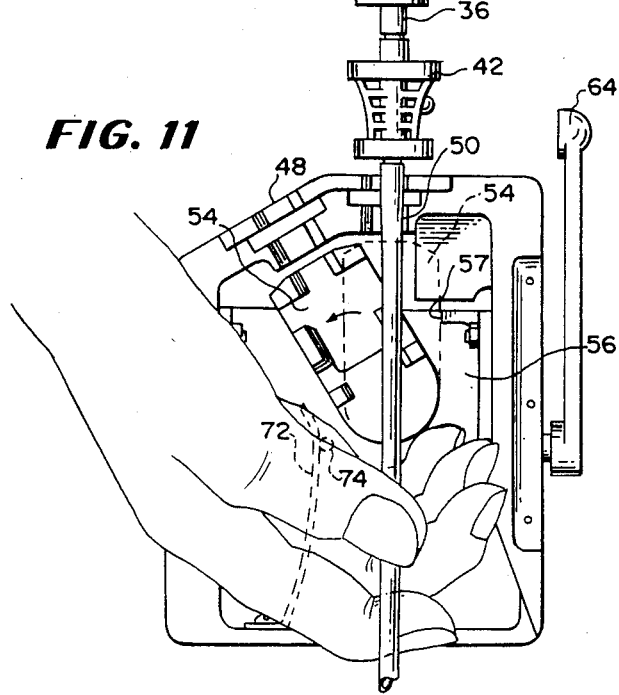
FIG. 11

CONNECTION DEVICE

FIELD OF THE INVENTION

Invention relates to devices intended to join and separate mating connectors, particularly in the medical field.

BACKGROUND OF THE INVENTION

In various fields, there is a need to repeatedly make and break connections between mating connectors. In many of these applications, it is also desirable to maintain aseptic conditions while the connections are being made and broken. This is particularly true in the medical field.

For example, during Continuous Ambulatory Peritoneal Dialysis (CAPD), a series of connections must be made four times a day between tubing which communicates with the peritoneal cavity and a source of peritoneal dialysis solution. Substantially sterile or aseptic techniques should be followed, if the risk of peritonitis is to be minimized. In many cases, patients undergoing CAPD lack dexterity and/or are physically debilitated, making it all the more difficult to make the connections and disconnections in the proper manner.

In response to this, automatic systems for making and breaking connections in the practice of CAPD have been provided.

For example, the Steri-Track device has been used and is described in an article entitled "CAPD For the Blind" from the periodical *Nephrology Nurse*, March/April 1981, pp. 53-54.

Other devices for making and breaking connections in the practice of CAPD are disclosed in Kulin et al U.S. Pat. No. 4,500,788 and Munsch et al U.S. Pat. No. 4,541,829, both of which are assigned to the assignee of the present invention.

SUMMARY OF THE INVENTION

The invention provides an improved device which makes and breaks connections between two connectors in an aseptic fashion and with a minimum of effort from the user.

The device comprises first, second, and third holders. Each of the holders is intended to carry a connector. The connector carried the third holder mates with either connector carried in the first and second holders.

In accordance with the invention, the position of the first and second holders is fixed, while the third holder is movable in a predetermined manner relative to the first and second holders.

More particularly, the third holder is movable in one path between an advanced position closely adjacent to the first and second holders and a retracted position spaced away from the first and second holders. The third holder is also movable in another path between a first position generally facing the first holder and a second position generally facing the second holder.

In accordance with one aspect of the invention, when the third holder is in its advanced position, it is retained in its first position. The first and third holders are thereby situated in a closely adjacent and mutually aligned relationship. Thus, while still coupled together, the first and third connectors can be loaded into the first and third holders.

In accordance with another aspect of the invention, as the third holder is moved from its advanced position toward its retracted position, the first and third connectors are uncoupled. In addition, the third holder is displaced from its first position into its second position. Thus, when the third holder is in its retracted position, the second and third holders and the connectors they carry are situated in a separated but properly aligned relationship.

In accordance with still another aspect of the invention, as the third holder is moved from its retracted position back toward its advanced position, the third holder is maintained in the second position. The desired alignment between the second and third connectors is thereby retained as these connectors are joined. However, when the now-coupled second and third connectors are removed from their respective holders, the third holder automatically returns back toward to its first position, again placing the first and third holders in a closely adjacent and aligned relationship.

Thus, in accordance with another aspect of the invention, upon completion of its sequence of operation, the device automatically readies itself to repeat another operating sequence just described.

Other features and advantages of the invention will be pointed out in, or will be apparent from, the specification and claims, as will obvious modification of the embodiments shown in the drawings.

BRIEF DESCRIPTION OF THE DRAWINGS

FIG. 2 is an exploded perspective view of the device shown in FIG. 1;

FIG. 3 is a further exploded perspective view of the shuttle and associated holder of the device shown in FIG. 2;

FIG. 4 is a top view of the device shown in FIG. 1 with the cover closed, a portion of which has been broken away, with the holder located in its first and advanced positions closely adjacent to and aligned with another holder located on the device;

FIG. 5 is a top view of the device shown in FIG. 1 with the cover closed, a portion of which has been broken away, with the holder located in its second and retracted positions separated from and aligned with yet another holder located on the device;

FIGS. 7 through 11 are top views of the device showing its operation during a typical CAPD exchange procedure.

Figure 1:
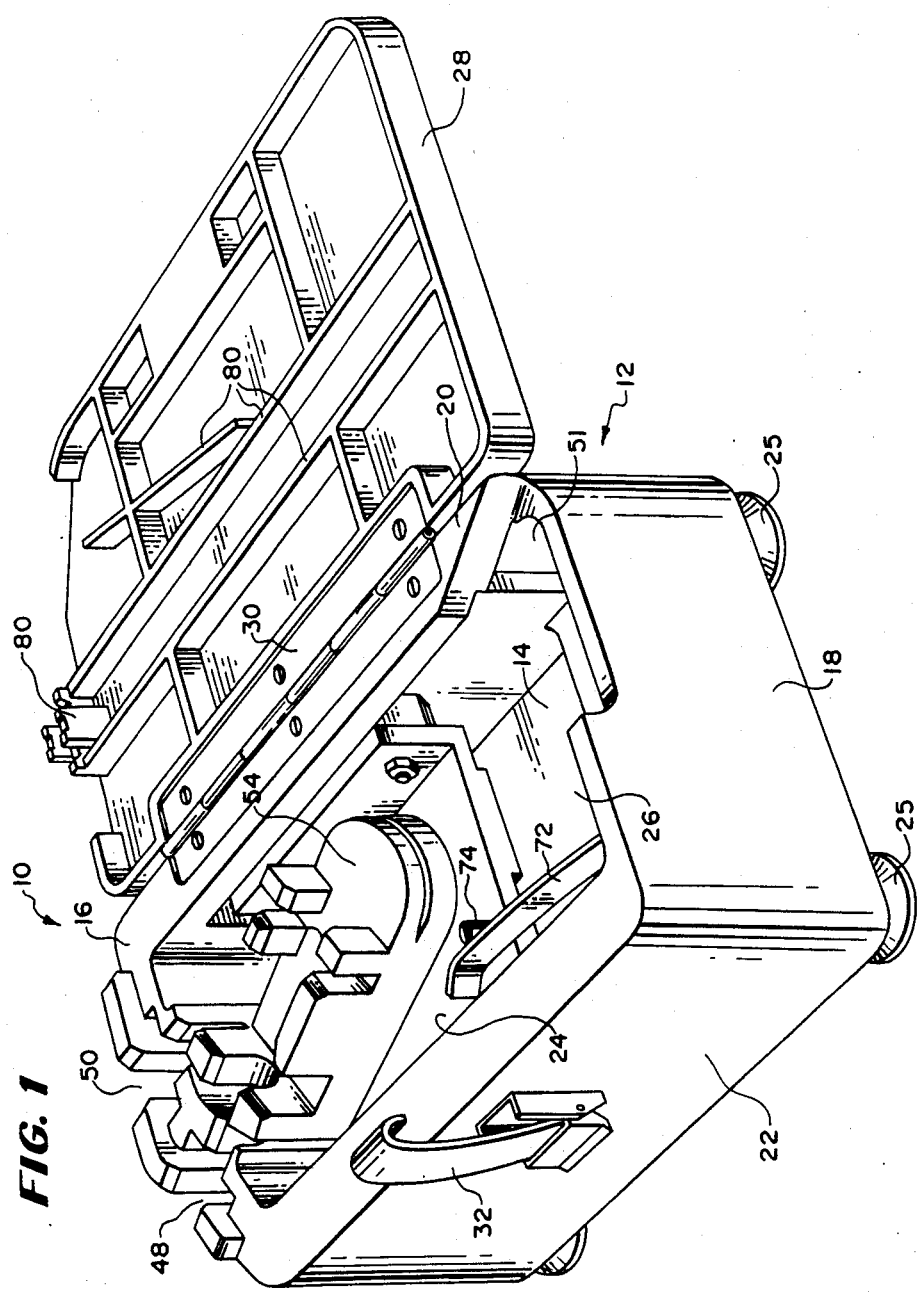
FIG. 1 is an assembled perspective view of a connection device which embodies the features of the invention.

Before explaining the embodiments of the invehtion in detail, it is to be understood that the invention is not limited in its application to the details of construction and the arrangement of components as set forth in the following description or as illustrated in the accompanying drawings. The invention is capable of other embodiments and of being practiced or carried out in various ways. Furthermore, it is to be understood that the phraseology and terminology employed are for the purpose of description and should not be regarded as limiting.

DESCRIPTION OF THE PREFERRED EMBODIMENTS

A device 10 for making and breaking connections between mating connection members is shown in the drawings. The device 10 can be used in a diverse number of environments both in the medical field and elsewhere. In the illustrated embodiment, the device is shown in the context of being used in the practice of CAPD.

Referring first to FIGS. 1 and 2, the device 10 includes a housing 12 having a base 14 and four upstanding sidewalls 16, 18, 20, and 22. An interior cavity 24 is formed having an open top 26.

A cover 28 is attached by a hinge 30 along one of the sidewalls 20. The cover 28 is movable between opened and closed positions. In the opened position (as shown in FIG. 1), access into the confines of the interior cavity 24 is permitted. In the closed position (as shown in FIGS. 2, 4 and 5), such access is prevented. A latch 32 is provided for releasably holding the cover 28 in its closed position.

Legs 25, each preferably with a gripping mechanism such as suction cups, hold the device 10 in place during use.

The housing 12 can be made of various materials and formed by various means. For example, it can be formed of molded plastic parts. Alternately, it can be formed of machined metal parts, or a combination of metal or plastic parts. The housing is preferably sized to be conveniently carried in one hand.

The device 10 receives and holds three mating connectors. In use, the device 10 breaks the connection between two of the connectors and forms a new connection between one of the parted connectors and the remaining third connector.

The particular configuration of the device 10 will vary according to the type of connectors used. In the illustrated embodiment (see, in particular, FIG. 7), two of the mating connectors comprise tubular sleeves which are attached to solution containers 38 and 40. These sleeves define access ports 34 and 36 for the associated solution containers 38 and 40.

Also in the illustrated embodiment, the other one of the mating connectors comprises a conventional spike member 42 which is carried at the end of tubing 44. In the context of CAPD, the tubing 44 communicates with the peritoneal cavity of the patient.

The spike member 42 carries a pointed end 43 which is intended to mate with either port 34 or 36. In use, the end 43 punctures a diaphragm 46 initially located in each port 34 or 36 (shown in phantom lines in port 36 in FIG. 7). Once the diaphragm 46 is pierced, the joined spike 42 and port 34 or 36 opens fluid communication between the associated solution container 38 or 40 and the peritoneal cavity of the patient.

Once these connections have been made, fresh peritoneal dialysis solution can be introduced into the peritoneal cavity for a desired dwell period and then drained, when spent, from the peritoneal cavity back into the original solution container 38 or 40. This exchange sequence is followed four times a day.

First and second holders 48 and 50 are arranged on the housing 12. In the illustrated embodiment, the holders 48 and 50 are both located along one of the sidewalls 16 of the housing 12, although other arrangements can be used.

The holders 48 and 50 can be variously constructed, depending upon the particular construction of the connectors they are intended to carry. In the illustrated embodiment, the holders each take the shape of a generally U-shape trough which is configured to receive an annular flange 52 formed on the ports 34 and 36 (see, for example, FIG. 7).

The first and second holders 48 and 50 can be situated on the housing 12 in various ways. In the illustrated embodiment, the axes of the first and second holders 48 and 50 are disposed generally at an acute angle to each other. Because of this, the portion of the sidewall 16 in which the first holder 48 is located is angled relative to the portion of the sidewall 16 in which the second holder 50 is located.

A third holder 54 is also located on the housing 12. In accordance with one aspect of the invention, the third holder 54 is movable toward and away from the holders 48 and 50. In the context of the illustrated embodiment, the third holder 54 moves in a linear path transversely within the interior cavity. 24 transversely between the sidewalls 16 and 18 between an advanced, or forward, position and a retracted, or rearward, position. In the forward position (see FIG. 4), the third holder 54 is adjacent to the sidewall 16 and the holders 48 and 50 formed thereon. In the rearward position (see FIG. 5), the third holder 54 is closely adjacent to sidewall 18, spaced away from the sidewall 16 and thus separated from the associated holders 48 and 50.

The third holder 54 can be variously constructed, again depending upon the particular construction of the associated connector. In the illustrated embodiment, the third holder 54 is configured to receive and hold the spike member 42 with the pointed end 43 of the spike member 42 generally facing in the direction that the holder 54 is moved into its forward position. The sidewall 18 of the housing includes an opening 51 through which the tubing 44 associated with the spike member 42 passes into the confines of the housing cavity 24.

Movement of the third holder 54 inside the interior cavity 24 of the housing 12 can be variously accomplished. In the illustrated embodiment, the third holder 54 is carried by a shuttle 56. The shuttle 56 is movable between the forward position and the rearward position.

A mating rack 58 and gear 60 move the shuttle 56. The rack 58 is attached to and moves with the shuttle 56. The gear 60 is mounted on the base 14 of the housing 12 (see FIG. 2).

The gear 60 rotates about a shaft 62, which terminates in a handle 64. As the handle 64 is rotated, the gear 60 also rotates, and the rack 58 is moved. The attached shuttle 56 thus moves transversely in a linear path between the already described forward and rearward position.

The third holder 54 is also movable in another path relative to the holders 48 and 50. More particularly, the third holder 54 is movable between a first position (shown in FIG. 4), in which the front edge 55 of the third holder 54 is generally pointed toward the first holder 48, and a second position (shown in FIG. 5), in which the front edge 55 of the third holder 54 is generally pointed toward the second holder 50.

While this manner of movement can be variously accomplished, in the illustrated embodiment (see FIG. 3), the third holder 54 includes a pivot pin 66 attached by a screw 68 to the shuttle 56. The third holder 54 thus rotates about this pivot pin 66 between the heretofore described first and second positions.

Thus, in the illustrated embodiment, the third holder 54 moves between its forward and rearward positions in a linear path which is transverse its axis of rotation (i.e., pivot pin 66) between its first and second positions.

It should be appreciated that, alternatively, the third holder 54 can be moved in a linear path between its first and second position, depending upon the particular relative placement of the holders 48, 50, and 54.

In accordance with another aspect of the invention, when the third holder 54 occupies its forward position, the holder 54 is retained in its first position. The third holder 54 is thus situated in closely adjacent alignment with the first holder 48 (see FIG. 4.

The third holder 54 can be retained in its first position in various ways. In the illustrated embodiment (see FIG. 3), a torsion spring 70 is used. One end 70a of the torsion spring 70 is fitted within a hole 71 drilled in the shuttle 56, while the other end 70b of the torsion spring 70 is in operative engagement with the third holder 54. The torsion spring 70 is in a relaxed state when the holder 54 is in its first position (see FIG. 4). Movement of the holder 54 toward the second position (see FIG. 5) places the torsion spring 70 in tension. The torsion spring 70 thus serves to bias the third holder 54 toward its first position.

In accordance with another aspect of the invention, as the third holder 54 is moved from its forward position into its rearward position, the third holder 54 is moved from its first position into its second position. Thus, when the third holder 54 is in its rearward position, the third holder 54 is situated in a separated and aligned relationship with the second holder 50 (see FIG. 5).

While this mechanism can be variously accomplished, in the illustrated embodiment, a leaf spring 72 is attached to the sidewall 18 and extends into the interior cavity 24 of the housing 12. When the third holder 54 is in its forward position, the leaf spring 72 is held by a pin 74 carried by the shuttle 56 away from operative contact with the third holder 54. The torsion spring 70 thus acts without interference to bias the third holder 54 toward its first position, as shown in FIG. 4.

However, as the third holder 54 is moved from its forward postion toward its rearward position (see FIG. 5), the shuttle pin 74 is moved progressively along and ultimately away from contact with the leaf spring 72. At the same time, the third holder 54 is moved into progressive operative contact with the leaf spring 72. The force of the leaf spring 72 is such that it overcomes the force of the torsion spring 70. The third holder 54 is thus progressively displaced by the leaf spring 72 from its first position toward its second position against the action of the torsion spring 70. When the third holder 54 has reached its rearward position, the holder 54 is held in its second position between the leaf spring 72 and a shoulder 57 formed on the shuttle 56. In this position, the third holder 54 is mutually aligned with the second holder 50 (see FIG. 5).

The operation of the device 10 in the context of a CAPD exchange procedure will now be described, with reference principally to FIGS. 7 to 11.

During the course of a typical CAPD exchange procedure, the patient first drains spent dialysis solution from his or her peritoneal cavity into the empty bag 38 through the connection already formed between the coupled first and third connectors 34 and 42. The first and third connectors 38 and 42 were initially coupled together when the bag 38, then full of fresh peritoneal dialysis solution, was first connected to the tubing 44 to introduce the fresh solution into the peritoneal cavity.

After bag 38 is filled with the spent solution, a clamp 76 is attached to close off the port connector 34.

The patient now commences to use the device 10 to disconnect the bag 38 of spent solution from the spike member 42 and to connect to the same spike member 42 the bag 40 of fresh solution.

Figure 7:
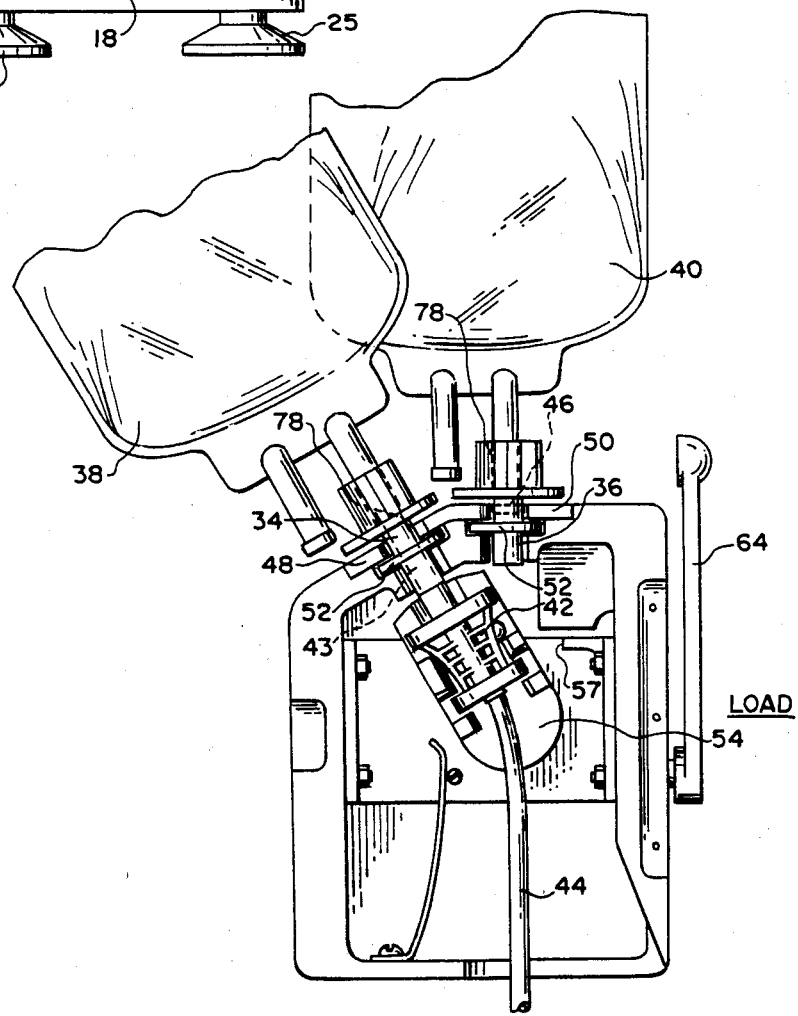

As shown in FIG. 7, with the third holder 54 in its forward position, the cover 28 is opened, and the patient loads the still-coupled first and third connectors 34 and 42 into the first and third holders 48 and 54. Because the third holder 54 is retained by its normal bias in its first position (as shown in FIG. 7), and because the two holders 48 and 54 are now also closely adjacent to each other, the first and third connectors 34 and 42 can be conveniently loaded while in a coupled relationship into the device 10. Absent movement of the third holder 54, the connectors 34 and 42 are held in this coupled relationship.

As shown in FIG. 7, while the cover 28 is still open, the second connector 36 is also placed into the second holder 50. The second connector 36 is associated with the bag 40 of fresh peritoneal dialysis solution. A clamp 78 is attached to initially close off the port tube, which is also internally sealed by the diaphragm 46.

The cover 28 is now closed, enclosing the connectors 34, 36, and 42 within the confines of the housing 12.

Now, as shown in FIG. 8, the third holder 54 is moved from its forward position toward its rearward position. As the third holder 54 first begins to move away from the first holder 48, the leaf spring 72 still rests against the pin 74. The holder 54 is thus still biased, due to the torsion spring 70, toward its first position. The relative movement between the two connectors 34 and 42 at this point thus serves to pull the connectors 34 and 42 apart.

However, once the connection is broken and advancement of the third holder 54 continues, the pin 74 is eventually moved away from the leaf spring 72. Progressive contact is made between the third holder 54 and the leaf spring 72. The third holder 54 is moved by the leaf spring 72, overcoming the action of the torsion spring 70, from its first position toward its second position. When the third holder 54 reaches its rearward position, the third connector 42 has been aligned with the second connector 36, the two connectors 36 and 42 still being in an uncoupled relationship.

Now, as shown in FIG. 9, the third holder 54 is next moved from its rearward position back toward its forward position. As seen in FIG. 9, contact between the pin 74 and the leaf spring 72 does not occur until the tip 43 of the third connector 54 enters the second connector 36. Thus, until the desired degree of engaging contact is made between the two connectors 36 and 42, the leaf spring 72 continues to bear against the third holder 54, retaining it in its second position in the desired alignment with the second holder 50.

Now, as shown in FIG. 10, further advancement of the third holder 54 into its forward position completes the connection between the third connector 42 and the second connector 36, causing the spike tip 43 to pierce the diaphragm 46. During this operation, the leaf spring 72 is completely lifted away from the third holder 54 by the pin 74. At this point, the interlocked relationship between the second and third connectors 36 and 42 still holds the third holder 54 in its second position against the action of the torsion spring 70.

Now as shown in FIG. 11, the cover 28 is opened, and the coupled second and third connectors 36 and 42 are removed from the device 10. Upon their removal, the third holder 54 automatically returns back to its first position by the action of the torsion spring 70, which now unopposed.

The patient can now proceed to open the clamp 78 and introduce the fresh dialysis solution from the bag 40 into his or her peritoneal cavity through the now connected second and third connectors 36 and 42. The other bag 38 and associated connector 36 is also removed and discarded.

A CAPD exchange procedure using the device 10 is now complete. As can be seen in FIG. 11, due to the features of the invention, the device 10 has automatically readied itself for use in another exchange procedure, following the same sequence of operation just described.

Figure 6:
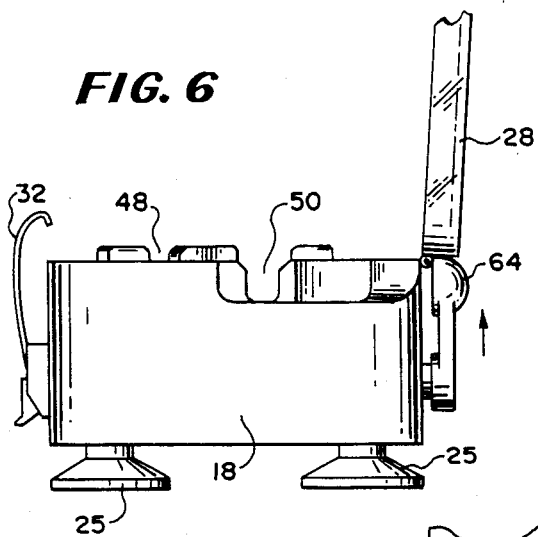
FIG. 6 is an end view of the device, showing the cooperative relationship between the handle and the cover of the device.

Preferably, as above described, the cover 28 should be closed while the connections are being broken and remade. To assure this, in the preferred embodiment, the handle 64 and cover 28 cooperate to require the operation to close the cover 28 before the handle 64 can be manipulated to move the third holder 54. More particularly, as shown in FIG. 6, when the cover 28 is opened, it will prevent the movement of the handle 64 required to operate the device 10. Thus, the operator is not able to operate the device 10 to manipulate the connectors unless the cover 28 is closed.

Also in the preferred embodiment, as shown in FIG. 1, the cover 28 includes a series of shoulders 80 formed along the predetermined tracks of movement of the third holder 54 within the housing 12. These shoulders 80 prevent accidental dislodgement of the connectors out of their respective holders 48, 50, and 54 during use, for example, should the device 10 be accidentally turned on its side or upside down.

If desired, a source of ultraviolet radiation (not shown) may be placed within the interior cavity 24 of the device 10 to provide a sterilizing function.

Various features of the invention are set forth in the following claims.

We claim:

1. A device for sequentially uncoupling two mating connectors and then forming a new coupling between one of the connectors and another mating connector, said device comprising a housing, a first holder on said housing for carrying a first connector, a second holder on said housing for carrying a second connector, a third holder on said housing for carrying a third connector which mates with either of the first or second connectors, said third holder being movable between an advanced position adjacent to said first and second holders and a retracted position spaced away from said first and second holders, first means for normally biasing said third holder toward a first position in operative alignment with said first holder when said third holder is in said advanced position so that the first and third connectors can be carried in said first and third holders in a coupled relationship, second means operative in response to movement of said third holder from said advanced position toward said retracted position for uncoupling the first connector carried in said first holder from said third connector carried in said third holder and for moving said third holder against the action of said first means into a second position in operative alignment with said second holder so that, when said third holder is in said retracted position, the third connector carried in said third holder is positioned in a spaced apart and operatively aligned relationship with the second connector carried in said second holder, and third means operative in response to movement of said third holder from said retracted position toward said advanced position for maintaining said third holder against the action of said first means in said second position to couple the second connector carried in said second holder with the third connector carried in said third holder and for automatically returning said third holder to said first position upon removal of the now-coupled second and third connectors from said respective holders.

2. A device for sequentially uncoupling two mating connectors and then forming a new coupling between one of the connectors and another mating connector, said device comprising a housing, a first holder on said housing for carrying a first connector, a second holder on said housing for carrying a second connector, a third holder on said housing for carrying a third connector which mates with either of the first or second connectors, said third holder being movable between an advanced position adjacent to said first and second holders and a retracted position spaced away from said first and second holders, first means for retaining said third holder in a first position in operative alignment with said first holder when said third holder is in said advanced position so that the first and third connectors can be carried in said first and third holders in a coupled relationship, second means operative in response to movement of said third holder from said advanced position toward said retracted position for uncoupling the first connector carried in said first holder from said third connector carried in said third holder and for moving said third holder into a second position in operative alignment with said second holder so that, when said third holder is in said retracted position, the third connector carried in said third holder is positioned in a spaced apart and operatively aligned relationship with the second connector carried in said second holder, and third means operative in response to movement of said third holder from said retracted position toward said advanced position for maintaining said third holder in said second position to couple the second connector carried in said second holder with the third connector carried in said third holder and for automatically returning said third holder to said first position upon removal of the coupled second and third connectors from said respective holders.

3. A device according to claim 1 or 2
wherein said housing includes sidewalls, and
wherein said first and second holders are located on one of said sidewalls.

4. A device according to claim 3
wherein said first and second holders each includes an axis, and
wherein said first holder axis is located at an angle relative to said second holder axis.

5. A device according to claim 1 or 2 wherein said housing includes two oppositely spaced sidewalls, wherein said first and second holders are located on one of said oppositely spaced sidewalls, and wherein said third holder is movable transversely between said oppositely spaced sidewalls, said advanced position being generally adjacent to said one oppositely spaced sidewall and said retracted position being generally adjacent to the other one of said oppositely spaced sidewalls.

6. A device according to claim 1 or 2 and further including a shuttle movable between said advanced and retracted positions, wherein said third holder is carried by said shuttle between said advanced and retracted positions, and wherein said third holder is movable relative to said shuttle between said first and second positions.

7. A device according to claim 6 wherein said third holder rotates about a rotational axis between said first and second positions.

8. A device according to claim 7 wherein said shuttle is movable in a linear direction transverse of said rotational axis of said third holder between said advanced and retracted position.

9. A device according to claim 1 or 2 wherein said third holder rotates about a rotational axis between said first and second positions.

10. A device according to claim 9 wherein said third holder is movable in a linear direction transverse of said rotational axis between said advanced and retracted position.

11. A device according to claim 1 or 2 wherein said first means includes a spring.

12. A device according to claim 1 or 2 wherein said second means includes spring means for making operative contact with said third holder to move said third holder from said first position to said second position as said third holder is moved into said retracted position.

13. A device according to claim 12 wherein said second means includes pin means operatively associated with said spring means for preventing said operative contact between said spring means and said third holder until after said third holder has been advanced sufficiently toward said retracted position to uncouple the first and third connectors.

14. A device according to claim 1 or 2 wherein said third means includes spring means for making operative contact with said third holder to maintain said third holder in said second position as said third holder is moved from said retracted position toward said advanced position.

15. A device according to claim 14 wherein said third means includes pin means operatively associated with said spring means for terminating said operative contact between said spring means and said third holder when said third holder has been advanced sufficiently toward said advanced position to cause contact between the second and third connectors, whereupon said contact between the second and third connectors maintains said third holder in said second position.

16. A device according to claim 15 wherein said third means includes bias spring means for automatically moving said third holder from said second position to said first position upon removal of the coupled second and third connectors from said respective holders.

17. A device according to claim 16 wherein said first means and said bias spring means of said third means comprise the same spring.

18. A device for sequentially uncoupling two mating connectors and then forming a new coupling between one of the connectors and another mating connector, said device comprising a housing, a first holder on said housing for carrying a first connector, a second holder on said housing for carrying a second connector, a third holder on said housing for carrying a third connector which mates with either of the first or second connectors, said third holder being movable between an advanced position adjacent to said first and second holders and a retracted position spaced away from said first and second holders, first spring means for normally biasing said third holder toward a first position in operative alignment with said first holder when said third holder is in said advanced position so that the first and third connectors can be carried in said first and third holders in a coupled relationship, second spring means operative during movement of said third holder from said advanced position into said retracted position for operatively contacting said third holder to move said third holder against the action of said first spring means from said first position into a second position in operative alignment with said second holder so that, when said third holder is in said retracted position, the third connector carried in said third holder is positioned in a spaced apart and operatively aligned relationship with the second connector carried in said second holder, said second spring means being further operative during movement of said third holder from said retracted position toward said advanced position for maintaining said third holder in said second position against the action of said first spring means, pin means operatively associated with said second spring means for preventing said operative contact between said second spring means and said third holder during movement of said third holder from said advanced position toward said retracted position until after said third holder has been advanced sufficiently toward said retracted position to uncouple the first and third connectors and for terminating said operative contact between said second spring means and said third holder during movement of said third holder from said retracted position toward said advanced position when said third holder has been advanced sufficiently toward said advanced position and to cause contact between the second and third connectors, whereupon said contact between the second and third connectors maintains said third holder in said second position as the second and third connectors are coupled together, and said first spring means being operative, upon removal of the coupled second and third connectors from said second and third holders, for automatically returning said third holder to said first position.

19. A device according to claim 18 wherein said housing includes two oppositely spaced sidewalls,
wherein said first and second holders are located on one of said oppositely spaced sidewalls, and
wherein said third holder is movable transversely between said oppositely spaced sidewalls, said advanced position being generally adjacent to said one oppositely spaced sidewall and said retracted position being generally adjacent to the other one of said oppositely spaced sidewalls.

20. A device according to claim 19
and further including a shuttle movable between said advanced and retracted positions,
wherein said third holder is carried by said shuttle between said advanced and retracted positions, and
wherein said third holder is movable relative to said shuttle between said first and second positions.

21. A device according to claim 20
wherein said third holder rotates about a rotational axis between said first and second positions.

22. A device according to claim 21
wherein said shuttle is movable in a linear direction transverse of said rotational axis of said third holder between said advanced and retracted position.

23. A device according to claim 20
wherein said pin means is carried by said shuttle.

* * * * *